United States Patent [19]

Decker

[11] Patent Number: 4,660,287
[45] Date of Patent: Apr. 28, 1987

[54] KNIFE WITH REPLACEABLE BLADE

[76] Inventor: John R. Decker, 5710 Harder St., San Jose, Calif. 95129

[21] Appl. No.: 794,202

[22] Filed: Nov. 1, 1985

[51] Int. Cl.⁴ .............................................. B26B 5/00
[52] U.S. Cl. ...................................... 30/339; 30/162; 30/335
[58] Field of Search ................. 30/162, 335, 336, 337, 30/339

[56] References Cited

U.S. PATENT DOCUMENTS

| | | | |
|---|---|---|---|
| 1,853,672 | 4/1932 | Dodson | 30/162 |
| 1,887,188 | 11/1932 | Ross | 30/162 |
| 2,291,514 | 7/1942 | Warner | 30/162 |
| 3,314,148 | 4/1967 | Foellmi | 30/162 |
| 3,381,807 | 5/1968 | DeVaughn | 30/162 X |
| 3,621,570 | 11/1971 | Kolde | 30/162 |
| 3,863,339 | 2/1975 | Reaney | 30/336 X |
| 4,570,342 | 2/1986 | Baum | 30/162 |

*Primary Examiner*—Jimmy C. Peters
*Attorney, Agent, or Firm*—Townsend and Townsend

[57] ABSTRACT

A knive having a tubular handle and provided with an open end for receiving a pair of blade clamping members in the form of leaf springs, one of the leaf springs being longer than the other leaf spring and having a projecting tab for insertion into a hole in the shank of a blade to be coupled to the handle. The inner end of the longer leaf spring is coupled to a slidable member having a knob projecting through and movable longitudinally of a slot in the handle. Movement of the slide member in one direction causes the projecting tab on the longer leaf spring to become exposed for coupling the blade shank to the leaf spring. Movement of the slide member in the opposite direction causes the longer leaf spring to be retracted fully into the handle so that the blade will be centered between the two leaf springs while projecting outwardly from the handle to expose the cutting edge of the blade. When the blade is in its operative position, the shank of the blade is in surface contact with and clamped between the adjacent surfaces of the two leaf springs. When the blade is separated from the handle, the two leaf springs bow toward each other. In one embodiment, the handle is metal. In another embodiment, the handle is plastic and the shorter leaf spring has a pair of side flanges at the outer end thereof to prevent damage to the plastic material of the handle when the blade is moved into its operative position.

20 Claims, 15 Drawing Figures

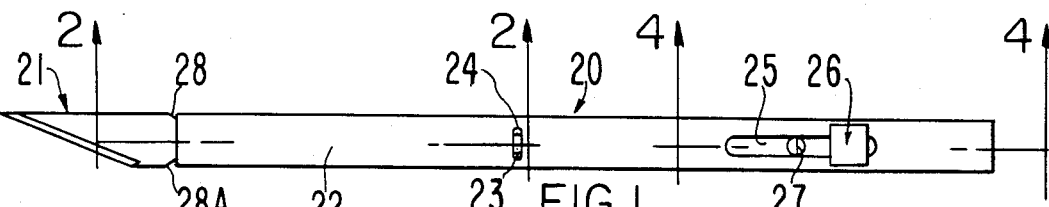
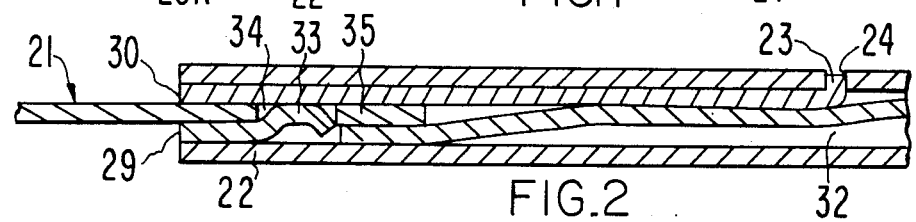
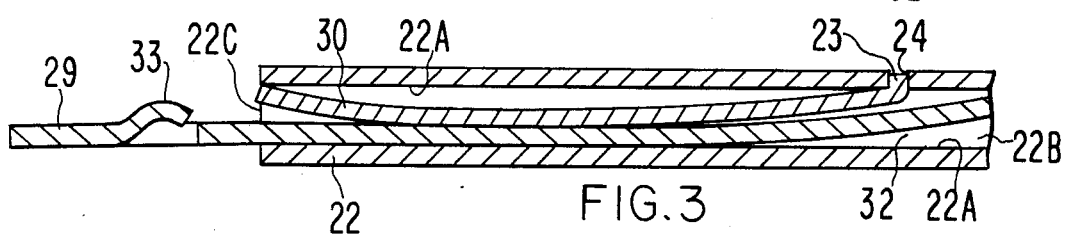
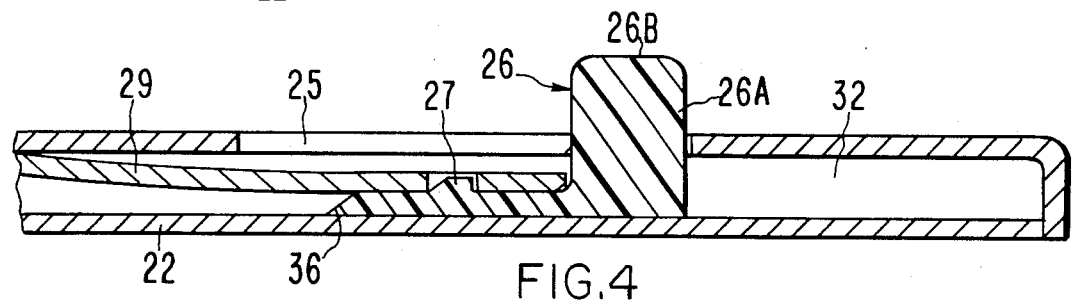
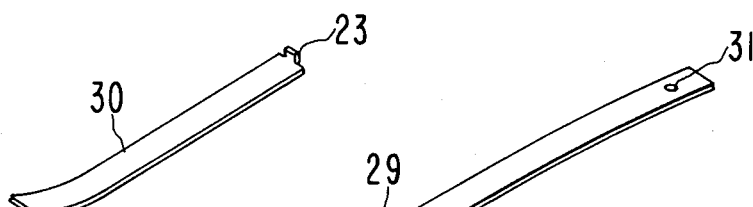
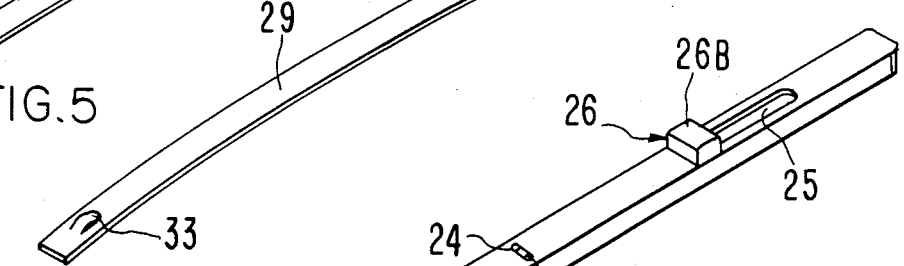
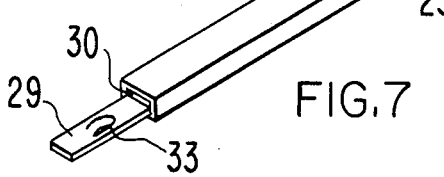
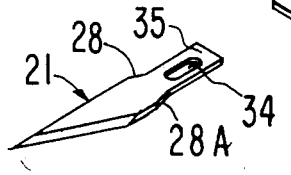

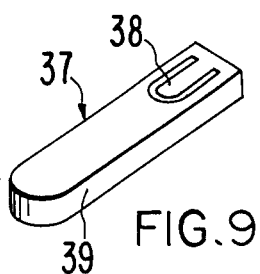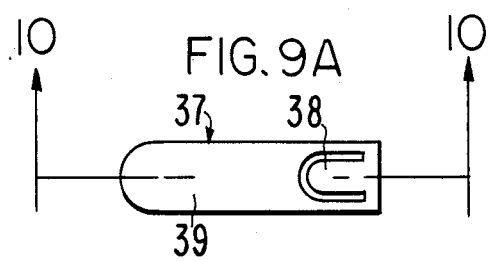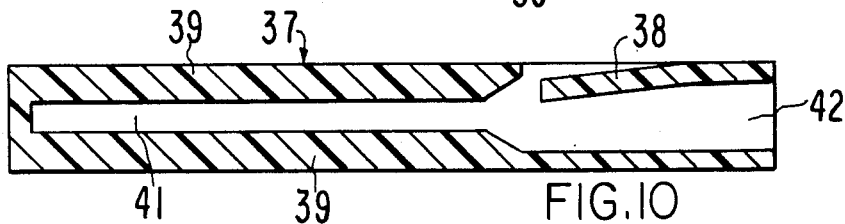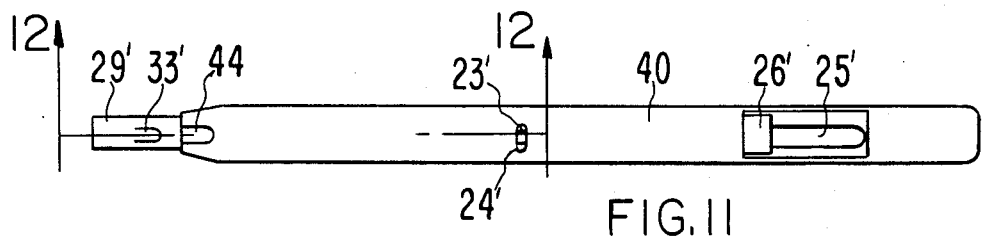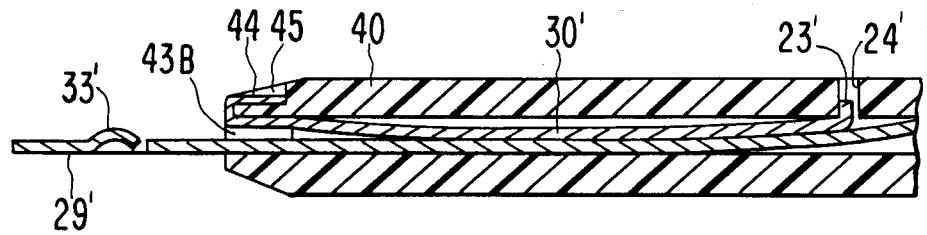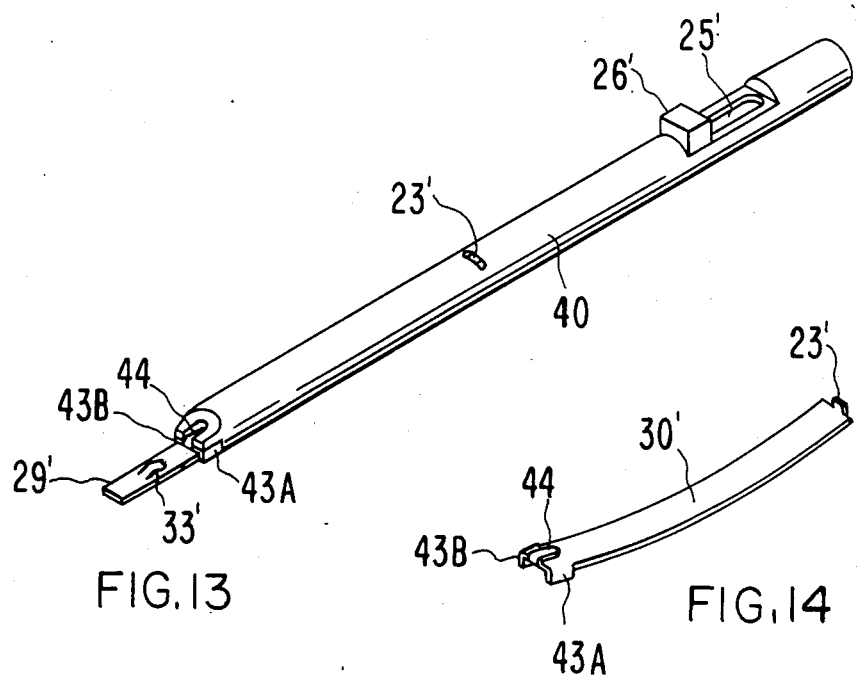

KNIFE WITH REPLACEABLE BLADE

This invention relates to knives of the type having removable blades, such as knives typically suitable for use in graphic arts work and the like.

BACKGROUND OF THE INVENTION

It is well known to provide a knife of the type having a handle and a flat blade removably coupled to and projecting outwardly from the handle at one end thereof. Such a knife is disclosed in U.S. patent application Ser. No. 615,922, filed May 31, 1984, now U.S. Pat. No. 4,646,440. A knife described in this disclosure includes a hollow handle open at one end thereof and provided with a spring steel blade carrier, slidably received within the handle. A blade is detachably secured to one end of the blade carrier and means is provided on the handle and coupled with the blade carrier for retracting the blade carrier into the handle so that the blade is moved partially into the handle and held firmly thereby so that the knife is then ready for immediate use. When the blade is so positioned, the blade carrier has a number of spaced surface portions thereon which engage the inner surface of the handle and the blade shank, thereby biasing the blade against the inner surface of the handle to firmly secure the blade in its operative position to the handle. The knife can then be used for a wide variety of different cutting and trimming tasks yet the blade can be quickly removed from the handle by sliding the blade carrier a short distance out of the handle itself and separating the blade from the handle.

While a knife of the aforesaid disclosure is extremely useful in many situations, it is possible that there might be objection to the fact that the blade is located off-center relative to the centerline of the handle when the blade is in its operative position on to the handle. This off-center mounting of the blade occurs because the blade carrier biases the shank of the blade against the inner surface of the handle. The present invention provides a knife of the type described which is constructed to eliminate such off-center mounting of the blade without sacrificing the advantageous features of the knife of the foregoing disclosure. objection.

SUMMARY OF THE INVENTION

The present invention is directed to a knife of the type described wherein the handle of the knife is open at one end for receiving therewithin a pair of leaf elongated blade-clamping members, at least one of the members being resilient. Preferably, both of the members are resilient and are in the form of leaf springs.

One of the leaf springs is longer than the other leaf spring, and the longer leaf spring has an inner end coupled to a slide member having a projection extending through a slot in the handle to permit manual shifting of the longer leaf spring between two positions. In one position, the longer leaf spring projects partially outwardly from the open end of the handle and, in the other position, the longer leaf spring is completely within the handle. The shorter leaf spring is normally in a fixed position within the handle body and normally bows toward and engages the longer leaf spring before a blade is coupled to the handle.

A blade having a shank is coupled to the handle by use of a projecting tab on the outer end of the longer leaf spring, such tab being removably received within a hole in the shank of the blade. Thus, when the tab is in the hole and when the slide member moves in a direction away from the open end of the handle, the blade shank is drawn into the handle and between the contiguous surfaces of the two leaf springs, whereby the leaf springs are in surface contact with both sides of the shank and the blade is effectively clamped between the leaf springs and centered with respect to the longitudinal axis of the handle body itself. In this way, the blade is held securely and there is a minimum of friction encountered between the blade, the leaf spring and the handle when drawing the blade into the handle body. When the blade is in its operative position on the handle, a pair of shoulders on the blade engage the end face of the handle, thereby further supporting the blade in place in its operative position.

The handle can be of metal or plastic. In either case, the handle preferably has a pair of opposed, flat inner surfaces which are engaged by the blade clamping members. If the handle is of plastic material, one of the blade-clamping members has a pair of side flanges at its outer end to protect the handle against being damaged when the blade is moved into and out of its operative position at one end of the handle.

The primary object of the present invention is to provide an improved knife with a replaceable blade wherein the blade, when in an operative position relative to the handle of the knife, is centered with respect to the longitudinal centerline of the handle itself yet the blade is securely coupled to the handle and the blade can be quickly and easily separated from the handle and the blade is located to provide a greater area for viewing the workpiece to be cut by the knife since the workpiece will not be obscured by the handle due to the centering of the blade.

Another object of the present invention is to provide a knife of the type described wherein the knife includes a tubular handle which can be of metal or plastic, the handle having a pair of blade clamping members therein, one of the members adapted to being releasably coupled to the shank of the knife blade so that, when the blade is drawn toward the knife handle by the one member, the blade is moved between the members and is effectively centered thereby, yet the knife is firmly but releasably attached to the handle in a manner such that there is no relative movement between the blade and the handle.

Other objects of this invention will become apparent as the following specification progresses, reference being had to the accompanying drawings for an illustration of the invention.

IN THE DRAWINGS

FIG. 1 is a side elevational view of the knife of the present invention showing the blade of the knife in its operative position extending outwardly from the open end of a metal handle;

FIG. 2 is an enlarged, fragmentary cross-sectional view taken along line 2—2 of FIG. 1;

FIG. 3 is a view similar to FIG. 2 but showing one of two blade clamping members in an extended position and ready to be coupled to the shank of the knife blade;

FIG. 4 is a cross-sectional view taken along line 4—4 of FIG. 1;

FIGS. 5 and 6 are perspective views of the two blade clamping members in the form of leaf springs;

FIG. 7 is a perspective view of the knife showing the blade separated from the extended end of one of the blade clamping members;

FIG. 8 is a perspective view of the slide member coupled to the inner end of the longer blade clamping member;

FIG. 9 is a perspective view of a protective cap for placement over the knife blade carried by the handle;

FIG. 9A is a top plan view of the protective cap shown in FIG. 9;

FIG. 10 an enlarged cross-sectional view taken along line of FIG. 9A;

FIG. 11 top plan view of the knife of the present invention, showing a handle made of plastic, the blade being removed;

FIG. 12 is an elarged, fragmentary cross-sectional view of the handle with the blade clamping members therein;

FIG. 13 is a perspective view of the knife shown in FIG. 11 with the blade removed; and FIG. 14 is a perspective view similar to FIG. 5 but showing another embodiment of the shorter of the two blade clamping members. The precision knife of the present invention is broadly denoted by the numeral 20 and is shown in FIG. 1 with a blade 21 releasably coupled thereto and projecting longitudinally therefrom at one end of the housing or handle 22. The blade has a cutting edge as shown in FIG. 1, such cutting edge extending at an angle with respect to the longitudinal centerline of the handle 22. The blade also has a shank 35 and a pair of shoulders 28 as shown in FIG. 7.

Handle 22 is hollow and is formed from metal, such as a suitable type of steel. The handle has an internal passage defined by a pair of flat, inner side surfaces 22a. Thus, handle 22 is adapted to receive a pair of blade clamping members 29 and 30, at least one of which is resilient. Preferably, both blade clamping members are resilient and in the form of leaf springs. The blade clamping members will hereinafter be referred to as leaf springs 29 and 30.

Leaf spring 29 is longer than leaf spring 30 as shown in FIGS. 5 and 6. One end of leaf spring 29 has a hole 31, and the other end of leaf spring 29 has a tab 33 integral with the leaf spring and projecting laterally therefrom as shown in FIG. 3. Tab 33 is adapted to be inserted into hole 34 (FIG. 7) of blade shank 35 when tab 33 is located exteriorly of the housing.

Leaf spring 30 has a lateral projection 24 at one end thereof and the leaf spring is normally curved or bowed in the manner shown in FIG. 3. Likewise, leaf spring 29 is curved or bowed.

Handle 22 has a generally rectangular cross-section to present a pair of opposed sides and a pair of opposed ends. One of the sides has a longitudinal slot 25 adapted to receive a shank 26a secured to a fingerlike handle 36 of a slide member 26. A knob 26b is mounted on the outer end of shank 26a and overlies slot 25 to allow manual movement of the slide member in either direction longitudinally of handle 22. Slide member 26 has a projection 27 which is adapted to be received in hole 31 of leaf spring 29.

To assemble knife 20, leaf springs 29 and 30 will be initially separate from handle 22. The first step is to insert leaf spring 30 into the open end of handle 22, the leaf spring being moved into the handle until tab 24 is received within aperture 23 as shown in FIG. 3. When this occurs, the outer end of leaf spring 30 engages the handle at the outer edge of the adjacent inner surface 22a near the open end of the handle as shown in FIGS. 2 and 3.

Slide member 26 is then inserted into slot 25 and leaf spring 29 is moved into handle 22 through the open end thereof until projection 27 is received within hole 31 (FIG. 6) of leaf spring 29. When the leaf springs are so positioned, they assume the shapes shown in FIG. 3 with the bow in leaf spring 30 in engagement with the adjacent surface portion of leaf spring 29 and forming a wedge-shaped entrance 22c for receiving the shank 35 of blade 21. The single bowed portion of leaf spring 29 engages the adjacent inner side surface 22a.

With slide member 26 at the position shown in FIG. 7, then the portion of leaf spring 29 having tab 33 projects outwardly from the open end of housing 22, thereby exposing tab 33 while leaf spring 30 remains in a fixed position within the handle 22 as shown in Fig. 3. Then, blade shank 35 is moved onto the exposed end of leaf spring 29 with tab 33 received within opening 34, following which slide member 26 is moved in the opposite direction by shifting knob 26b in a direction to the right when viewing FIG. 7. This action pulls blade 21 toward the handle 22 and shank 35 enters the housing and is lodged and clamped between leaf springs 29 and 30, as shown in FIG. 2. The thickness of leaf spring 29 is substantially the same as the thickness of leaf spring 30 so that blade 21 is effectively centered with respect to the longitudinal centerline of handle 22.

It can be seen from FIG. 2 that blade 21 is symmetrically located with reference to the sides of housing 22 yet the blade is effectively clamped between and is in surface engagement with the adjacent surface portions of leaf springs 29 and 30. The thickness of the blade is typically selected such that the two leaf springs and the blade effectively fill the space between the opposed sides 22a of handle 22 as shown in FIG. 2 so that there will be no relative movement between blade 21 and handle 22 to thereby provide a secure attachment of the blade to the handle 22. When so positioned, shoulders 28 of blade 21 engage the end face of handle 22 and provide a firm non-movable blade connection to the handle.

When it is desired to remove the blade, slide member 26 is moved to the left when viewing FIG. 4, causing leaf spring 29 to be moved into the position shown in FIG. 3, whereupon the blade can be separated from the leaf spring 29 by lifting the blade relative to and off tab 33. The blade can be replaced or merely removed from leaf spring 29, and leaf spring 29 be retracted into the handle 22 without the blade attached to it.

While handle 22 has been described above as being of metal, it could be of plastic as shown in FIGS. 11-13. The handle 40 in FIGS. 11-13 has a cylindrical outer surface and an inner passage with a rectangular cross section. Thus, handle 40 has flat inner surfaces for slidably engaging the leaf springs 29' and 30' substantially the same as leaf springs 29 and 30 as described above with respect to FIGS. 1-7 except that leaf spring 30' is slightly modified.

Leaf spring 30' has a pair of side flanges 43A and 43B (FIG. 14) which are located as shown in FIG. 12 when the leaf springs 29' and 30' are in their operative positions shown in FIG. 12. Flanges 43A and 43B protect the plastic material of the handle from being cut when the blade shank is moved into and out of the open end of the handle. Otherwise, the side edges of the blade shank would engage and cut the handle as the shank moves into and out of the handle.

Leaf spring 30' also has a tab 44 integral with the outer end thereof. This tab 44 is receivable in a recess 45 (FIG. 12) formed in the end of handle 40 to prevent lateral movement of leaf spring 30' when the blade is inserted in and removed from the handle.

It may be desirable to leave the blade attached to the handle during periods of nonuse. In such a case, it is desirable to provide a protective end cap 37 which is removably placed over blade 21 and engagable with the exposed flat sides of handle 22 near the open end of the handle. To this end, cap 37 has a tubular handle defined by a pair of spaced, flat sides 39 defining a blade-receiving chamber 41 therebetween. The sides are integral with each other at one end and at the side edges of the cap, the opposite end of the cap being open to allow placement of the cap over the blade 21. A tongue 38 is formed as an integral part of one of the sides 39 and the tongue is normally biased inwardly as shown in FIG. 11 so as to frictionally engage the adjacent side of handle 22 when the handle is removably received within the cap.

In use, the cap is mounted on handle 22 in covering relationship to blade 21. In such a position, the cap protects the user from injury due to being cut by the blade. The cap can be readily pulled away from handle 22 when it is desired to use the blade. At the end of the use of the blade, the cap is once again inserted over the blade and onto the end of the handle 22.

The present invention provides a precision knife which can be used for a number of different cutting operations, including those operations required to cut and trim in graphic arts work. A main feature of the knife is the fact that the blade 21 thereof is centered with respect to the longitudinal axis of the handle 22. Moreover, the use of the pair of leaf springs 29 and 30 assures that the blade is held securely without shifting from side to side or fore and aft with reference to the longitudinal axis of the blade itself. Furthermore, when drawing the blade shank into the housing when the shank is coupled to tab 33, a minimum of friction is encountered because of the minimal surface area of the leaf springs 29 and 30 which engaged the adjacent inner surface portions of the handle 22. The blade does not contact the handle at any time; thus, there is no friction involved between the blade and the handle during movement of the blade shank into and out of the housing.

Handle 22 has a thin profile and flat pattern cutouts are easier to achieve with the present invention because the viewing area is not obscured by the handle. This is enhanced by the fact that the blade is centered with respect to the handle. Thus, the knife can be used with a greater variety of cutting angles. The cap can be made of a clear polycarbonate material so as to be rugged in construction.

I claim:

1. A knife comprising:
   an elongated, hollow handle having an open end;
   a pair of elongated, reselient blade clamping members, at least one of said members being shorter in length than the other member, said members being within the handle, a first of said members being movable in the handle relative to the second member through a limited distance between a first position in which at least a major part of the first member is within the handle and a second position in which one end portion of the first member projects partially outwardly form the open end of the handle;
   a blade having a shank; and
   means on the first member for releasably coupling the shank of the blade to one side of the first member when the first member is in said second position, said blade being movable into a location in which the blade shank is within said handle and between said members as the first member moves into said first position, whereby the blade shank will be clamped between the members and the blade will be coupled with the handle when the first member is in said second position.

2. A knife as set forth in claim 1, wherein said members comprise leaf springs.

3. A knife as set forth in claim 1, wherein said handle has a slot, and means in said slot for moving the first member between the first and second positions.

4. A knife as set forth in claim 1, wherein the second member has a tab at the inner end thereof, said housing having a recess for removably receiving said tab, whereby the second member is releasably coupled to said handle.

5. A knife as set forth in claim 4, wherein the tab on said second member is at one end thereof, the opposite end of the second member being substantially adjacent to the open end of the handle.

6. A knife as set forth in claim 1, wherein the second member comprises a leaf spring and is bowed outwardly toward the first member.

7. A knife as set forth in claim 1, wherein the.first member includes a leaf spring having a tab thereon near the normally outermost end thereof, said tab defining said coupling means, said blade shank provided with a hole for removably receiving the tab.

8. A knife as set forth in claim 1, wherein the members are of substantially the same thickness, the width of the interior space of the handle being substantially equal to the sum of the thicknesses of the members and the blade shank, whereby the blade is centered with respect to the sides of the handle when the blade is coupled with the handle.

9. A knife as set forth in claim 1, wherein said first member has an inner end provided with a hole therethrough, and including a manually movable slide member in the handle and provided with a projection extending through the hole of the blade carrier.

10. A knife as set forth in claim 9, wherein the slide member has a shank, said handle having a slot for shiftably receiving the shank of the slide member, there being a knob on the outer end of the shank of the slide member for manual movement of the slide member relative to the slot.

11. A knife as set forth in claim 1, wherein the handle has a pair of opposed, flat sides.

12. A knife as set forth in claim 1, wherein the handle has a cylindrical outer surface.

13. A knife as set forth in claim 1, wherein is included a protective cap for removable placement over the knife and capable of being frictionally coupled to the handle.

14. A knife as set forth in claim 13, wherein the cap has an open end and a first chamber substantially complemental to the outer surface of the handle near the open end thereof, said cap further having a second chamber for receiving the blade, and surface means for frictionally engaging the handle when the blade is within the cap.

15. A knife as set forth in claim 1, wherein said members are leaf springs.

16. A knife as set forth in claim 15, wherein one of the leaf springs has an end tab, said handle having a recess for receiving the end tab to prevent lateral movement of said one leaf spring relative to the handle.

17. A knife as set forth in claim 15, wherein one of the leaf springs has a pair of side flanges near the open end of the handle.

18. A knife as set forth in claim 17, wherein said one leaf spring has an end tab, said handle having a recess for receiving the end tab to prevent lateral movement of said one leaf spring relative to the handle.

19. A knife as set forth in claim 18, wherein the handle is formed from a plastic material.

20. A knife as set forth in claim 18, wherein the flanges on said one leaf spring extend toward the other leaf spring.

* * * * *